US008816064B2

(12) United States Patent
Suh et al.

(10) Patent No.: US 8,816,064 B2
(45) Date of Patent: Aug. 26, 2014

(54) PURIFICATION OF NUCLEIC ACIDS

(75) Inventors: Chris Suh, San Jose, CA (US); Lee Hoang, Santa Clara, CA (US); Douglas T. Gjerde, Saratoga, CA (US)

(73) Assignee: PhyNexus, Inc., San Jose, CA (US)

( * ) Notice: Subject to any disclaimer, the term of this patent is extended or adjusted under 35 U.S.C. 154(b) by 36 days.

(21) Appl. No.: 13/250,040

(22) Filed: Sep. 30, 2011

(65) Prior Publication Data

US 2012/0083598 A1 Apr. 5, 2012

Related U.S. Application Data

(63) Continuation-in-part of application No. PCT/US2011/030232, filed on Mar. 29, 2011.

(60) Provisional application No. 61/388,460, filed on Sep. 30, 2010, provisional application No. 61/414,855, filed on Nov. 17, 2010.

(51) Int. Cl.
*C07H 21/00* (2006.01)
(52) U.S. Cl.
USPC ................ 536/25.42; 536/25.4; 536/25.41
(58) Field of Classification Search
None
See application file for complete search history.

(56) References Cited

U.S. PATENT DOCUMENTS

| | | |
|---|---|---|
| 5,747,663 A | 5/1998 | Colpan et al. |
| 5,990,301 A | 11/1999 | Colpan et al. |
| 6,180,778 B1 | 1/2001 | Bastian et al. |
| 6,242,220 B1 | 6/2001 | Wahle et al. |
| 6,274,371 B1 | 8/2001 | Colpan |
| 6,277,648 B1 | 8/2001 | Colpan |
| 6,297,371 B1 | 10/2001 | Colpan et al. |
| 6,383,393 B1 | 5/2002 | Colpan et al. |
| 6,821,757 B2 | 11/2004 | Sauer et al. |
| 6,946,250 B2 | 9/2005 | Bastian et al. |
| 7,074,916 B2 | 7/2006 | Bastian et al. |
| 2003/0007897 A1 * | 1/2003 | Creasey ................. 422/100 |
| 2005/0016921 A1 | 1/2005 | Gjerde et al. |
| 2005/0164260 A1 | 7/2005 | Chen |
| 2009/0227011 A1 | 9/2009 | Chen |
| 2010/0200509 A1 | 8/2010 | Suh et al. |

OTHER PUBLICATIONS

Yang et al. Journal of Biomolecular Techniques (2009), vol. 20, pp. 165-171.*
QIAprep Miniprep Handbook, 2nd Ed. Dec. 2006.

* cited by examiner

*Primary Examiner* — Patrick Lewis
(74) *Attorney, Agent, or Firm* — Sue S. Kalman

(57) ABSTRACT

The present invention solves the problem of isolating nucleic acids from cells in the presence of the growth medium. The invention is particularly useful for isolating extrachromosomal replicons such as plasmids. Cells are lysed in the presence of the medium in which they were grown and nucleic acids are isolated using a pipette tip column. A liquid handling robot can be used to isolate nucleic acids from multiple samples simultaneously without the need for human intervention.

7 Claims, 2 Drawing Sheets

PURIFICATION OF NUCLEIC ACIDS

CROSS REFERENCE TO RELATED APPLICATIONS

This application claims the benefit of U.S. Provisional Application No. 61/388,460, filed Sep. 30, 2010, U.S. Provisional Application No. 61/414,855, filed Nov. 17, 2010, and is a continuation-in-part of International Application No. PCT/US11/30232, filed Mar. 29, 2011, all of which are incorporated by reference herein.

BACKGROUND OF THE INVENTION

The present invention relates to parallel methods for isolating nucleic acids from cells, particularly self-replicating extrachromosomal DNA such as plasmid DNA. Commercially available formats for high-throughput purification of plasmid DNA include plates, spin columns and magnetic beads. Although attempts have been made to automate these technologies, they still employ a manual step of isolating cells from the medium in which they are grown, usually by centrifugation.

Conventional wisdom teaches that it is necessary to remove the growth medium from the cells before isolation of nucleic acid. In most plasmid preparation methods, the culture is centrifuged after growth and the spent medium supernatant is removed (see for example U.S. Pat. Nos. 6,277,648 and 6,297,371). This centrifugation step is not automated and requires human intervention, time and expense. Therefore, there exists a need for a fully automated method for preparation of plasmid DNA that does not require separation of cells from the growth medium. That is, there exists a need to recover plasmid DNA directly from a culture without the removal of the medium, associated byproducts, cell debris and other materials. The present invention fills this need and provides a fully automated method for nucleic acid isolation without centrifugation.

After the medium is removed, the next step in the isolation of nucleic acids is cell lysis and removal of cell debris, which is most often accomplished with a second centrifugation step. Conventional wisdom additionally teaches that this second centrifugation step is required for successful nucleic acid isolation. For example, U.S. Pat. No. 5,990,301, entitled "Process for the Separation and Purification of Nucleic Acids from Biological Sources" states that the problem of separating lysed cells from their contents is most effectively solved by centrifugation (column 6, lines 33-46). U.S. Pat. No. 6,368,800 entitled "Kits for Isolating Biological Target Materials using Silica Magnetic Particles", states that cellular debris is likely to interfere with the adhesion of nucleic acids to silica magnetic particles (column 10, lines 49-59). An automated method was developed to bypass this second centrifugation step which is the subject of international Application No. PCT/US11/30232, which is incorporated by reference herein.

SUMMARY OF THE INVENTION

The present invention solves the problem of isolating nucleic acids from cells in the presence of the growth medium. The invention is particularly useful for isolating extrachromosomal replicons such as plasmids.

The invention allows the user to save time, money and manual labor because the entire procedure can be automated. Cells are lysed in the presence of the medium in which they were grown, and nucleic acids are isolated using a pipette tip column engaged with a pipetting robot. Plasmid DNA can be isolated from multiple samples simultaneously without the need for human intervention. The method can be used to isolate plasmid DNA from 96 samples at a time.

DESCRIPTION OF SPECIFIC EMBODIMENTS OF THE INVENTION

Figure 1:
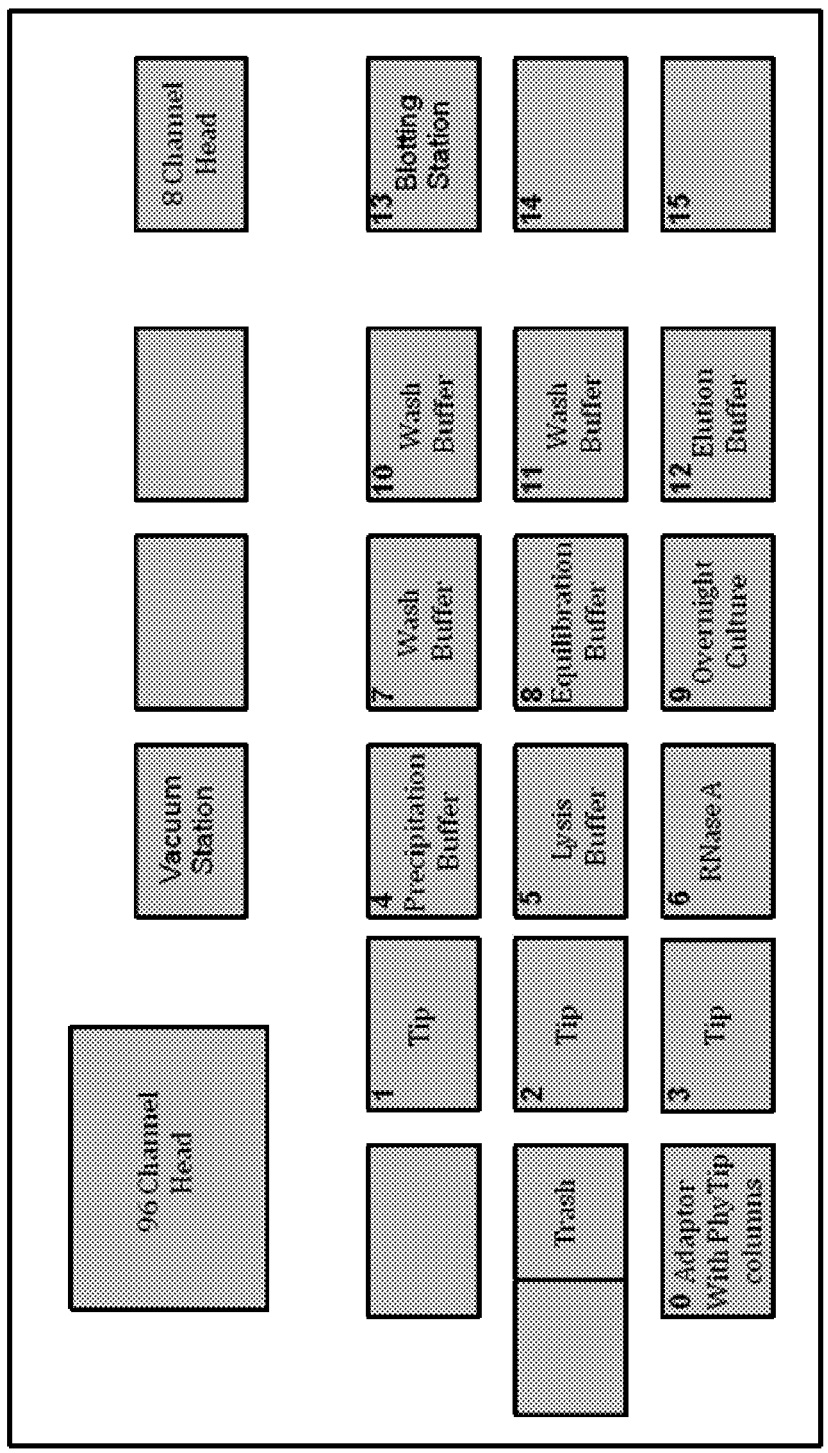
FIG. 1 depicts an embodiment of the layout used on the deck of a liquid handling robot.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

The invention is particularly useful for the isolation of small replicons such as plasmids. The invention involves a method of breaking open cells in a liquid culture and capturing plasmid DNA on a pipette tip column. In preferred embodiments, cell lysis is performed with alkali which requires subsequent neutralization. After lysis, chaotropic ions are added to the sample to promote binding to a silica solid phase in the column.

The method involves the following steps.
1. cell growth
2. cell lysis
3. precipitation of cell debris and other components
4. capture of plasmid DNA on a pipette tip column
5. elution of the purified plasmid All the method steps can be performed using automation in a 96-well format or another microplate format (e.g., 6, 12, 24, 48, 72 or 384 wells). Steps 1 through 3 can be performed using a single plate, which provides substantial savings of time, labor and the cost of disposables.

In prior art methods, the culture is centrifuged after growth, the medium is discarded and the cell pellet is resuspended in a buffer prior to alkaline lysis. Development of a method that bypasses this centrifugation step presented a number of technical challenges. For example, the spent growth medium present in the sample contains components that interfere with downstream processing including metabolic byproducts such as secreted proteins, endonucleases or carbohydrate. Alkaline lysis or the subsequent neutralization step could be less effective due to the buffering capacity or pH of the medium. Since each culture grows differently, the lysis and buffering of the culture is unpredictable. The RNase enzyme used during alkaline lysis might be less effective. Media components might compete with plasmid capture by binding the column matrix or by binding plasmid DNA. Media components might co-purify with the plasmids DNA, negatively impacting the purity of the purified plasmid.

In prior art methods, cell debris is removed after the lysis and neutralization steps to obtain a "clarified lysate" from which nucleic acids are purified. Removal of cell debris is most often accomplished by a second centrifugation step but can also be done with magnetic beads or filtration. Pipette tip purification of nucleic acids in the presence of cell debris was previously described in International Patent Application Number PCT/US11/30232 which is incorporated by reference herein.

However, in the present invention it is possible bypass both centrifugation steps and purify plasmid DNA without the removal of the growth medium or cell debris. This is remarkable in light of the fact that unpredictable behavior of plasmid DNA might occur in the presence of particulates and dissolved competing materials with one or more columns could make the method unreliable, unpredictable and unusable.

Because the cell debris removal step is omitted in the methods of the invention, the technological obstacles are compounded. Not only are media constituents present during plasmid purification, but cell debris is also present. The presence of cell debris in the sample can exacerbate the problems caused by media constituents and can additionally cause new problems. For example, the column could become clogged by particulates in the sample. If one or more of the columns becomes plugged, the method would not be robust. Cell debris could interfere with column binding the column, thus lowering yield or it could be purified along with the plasmid DNA, negatively impacting plasmid purity. In prior art methods, genomic DNA is often removed with cell debris, so the purified plasmid obtained from the present invention could contain genomic DNA or genomic DNA fragments.

In prior art methods, the culture is centrifuged after growth, the medium is discarded and the cell pellet is resuspended in a buffer. This prior art step has at least three advantages. First, the buffer conditions can be selected to optimize the downstream processing steps. Second, the culture can be concentrated, which effectively concentrates the plasmid, making it easier to capture while leaving more available volume in the well for the Lysis and Precipitation Buffers. Third, this step removes materials that could compete with the plasmid for binding the stationary phase in the column.

The invention is particularly useful for the isolation of small replicons such as plasmids (circular or linear) and phage DNA. A "plasmid" is defined herein as any replicon capable of autonomous replication within a suitable host. The invention is relevant to any organism that can harbor one or more plasmids. In some embodiments, the method is used for isolation of replicative form (RF) DNA from M13 or related bacteriophages. For simplicity, these replicons will be referred to herein as plasmids. Plasmids isolated by the methods of the invention can be engineered or they can be naturally occurring. They can be of low, medium or high copy number. In cases where the plasmids are engineered, they typically contain a selectable marker such as an antibiotic resistance gene. Other selectable markers can also be used, e.g., herbicide resistance genes.

To propagate cells harboring the plasmid, the cells are usually streaked onto a Petri plate containing the appropriate growth medium and selection. The plate is then incubated at the appropriate temperature for growth. Typically the plate is incubated overnight at 30 or 37° C. but other temperatures and incubation durations are also possible.

Using the methods of the invention, plasmids are isolated from a liquid culture. A liquid culture as defined herein is comprised of a growth medium and cells harboring the plasmid or plasmids to be isolated. It may also include an antibiotic as described below. A person skilled in the art can determine a suitable growth medium and conditions. Typically, liquid cultures are grown in a 96-well plate such as a 2.2 mL, deep-well plate at 37° C. with shaking (aeration).

In preferred embodiments, cells are grown using a rich and complex growth medium. Complex media are rich in nutrients and other components. They contain water soluble extracts of plant or animal tissue (e.g., yeast or beef extract, enzymatically digested animal proteins such as peptone and tryptone). Usually a sugar, often glucose is added to serve as the main carbon and energy source. The combination of extracts and sugar creates a medium which is rich in minerals and organic nutrients, but since the exact composition is unknown, the medium is defined as complex. A non-limiting list of complex growth media includes LB, Terrific Broth (TB), YT, 2X YT, Agencourt Ale (Beckman), EnPresso (Bio-Silta), SOC, Plasmid+ (Thomson Instrument Co.) and DNA-Gro™ (Expression Technologies, Inc.).

In other embodiments, a defined medium can be used. Defined media are media composed of pure ingredients in known concentrations i.e., the exact chemical composition of the medium is known. Typically, they contain a simple sugar as the carbon and energy source, an inorganic nitrogen source, various mineral salts and if necessary growth factors (purified amino acids, vitamins, purines and pyrimidines).

When the plasmid to be isolated contains a selectable marker, the liquid medium also includes selection. For example, if the plasmid is comprised of an ampicillin resistance gene, the medium could contain ampicillin ranging from approximately 20 mg/l to 500 mg/ml. More specifically, the medium might contain 50, 75, 100, 125, 150, 175, 200, 250 or 300 mg/ml of ampicillin.

Liquid cultures are usually inoculated from a single colony or plaque. The inoculation step can be done manually or in an automated fashion using a colony-picker or plaque picking robot. Cultures can be grown in a microplate having any number of wells including 384, 96, 48, 24, or 633. Any other growth formats can also be used such a flask, tubes or fermentor. When cultures are grown in a microplate, the plate can be covered with a breathable membrane.

Generally, bacterial cultures are grown at 37° C. and 300 rpm until late log phase, usually about 16 hours. Yeast cultures are typically grown at 30° C. A person of skill in the art can determine the optimum growth conditions for a particular host strain.

Referring to FIG. 1, the overnight culture is placed in position 9 on the robotic deck and RNase A from position 6 is added using the regular pipette tips from position 1. Because the procedure is automated in preferred embodiments, the times at which events are performed are predetermined and pre-programmed into the method.

Lysis

After cell growth, the first step in isolating plasmid DNA is usually the addition of an RNase such as RNase A. However, in some embodiments the RNase can be omitted. The final concentration of RNase is in the range of 0-1 mg/ml, or at least 0.1, 0.2, 0.3, 0.4, 0.5, 0.6, 0.7, 0.8, 0.9 or 1 mg/ml. Because of the buffering capacity and components present in the growth medium, the effective concentration of RNase must be determined for each set of culture conditions.

Lysis is typically done with a high pH and surfactant solution to break up the cellular wall and release the plasmid into solution. In order to capture plasmid DNA directly from culture, the first step would be to lyse the cells contained in culture to release the plasmid without first isolating the cells.

However, performing the lysis step in a liquid culture presents several potential problems. The culture contains many components including the medium, buffers, salts, secreted proteins, metabolic byproducts, carbohydrates, particulates and other products of growth, some of which are not identified or known. The presence and concentration of the various components in the culture could negatively impact the effectiveness of the lysis solution and control of the lysis process. Lysis might be incomplete and/or unpredictable. The chemical conditions and physical procedure required in an unpredictable process is unknown. Furthermore, RNase added to the culture may be ineffective or unpredictable. The cell concentrations within cultures are variable and the culture could contain compounds that prevent plasmid recovery. Genomic DNA that may be present may behave differently chemically and/or physically which could prevent plasmid purification or contaminate the final product. Any these components could interfere with or contaminate plasmids in an isolation process performed directly from culture. Considering these potential problems, it is remarkable that the column process of the invention could even be developed to capture plasmids direct from culture.

Lysis can be performed after the addition of RNase or concurrently. Lysis can be carried out by any means including the use of chemicals i.e., detergents or enzymes (e.g., lysozyme), or mechanical/physical means, such as sonication, homogenization or pressure. In preferred embodiments, lysis is carried out with alkali such as sodium hydroxide, potassium hydroxide or other bases or mixtures of alkaline reagents. As with the RNase, it may be necessary to use a higher concentration of base than that used in prior art methods due to the buffering capacity or components of the growth medium. When sodium hydroxide is used, the concentration can range from 10 mM to 17.6 M.

In these embodiments, detergent is also added at the time of lysis to help solubilize proteins and DNA. Any detergent can be used including sodium dodecylsulfate (SDS), Triton X-100, Tween, NP-40 or mixtures thereof. When SDS is used, the concentration typically ranges between 0.001% and 20% (v/v), preferably between 0.01 and 5%, and more preferably between 0.1 and 4%.

In the embodiment depicted in FIG. 1, a Lysis Buffer comprised of sodium hydroxide and SDS is in deck position 5 on the robotic instrument. A gentle mixing step follows the addition of the lysis buffer. The same pipette tip used for addition of the lysis buffer can be used for the mixing steps by repeatedly aspirating and expelling the mixture.

In preferred embodiments, only a portion of mixture is aspirated and expelled in the mixing procedure. This portion is less than 90%, less than 80% of the total volume and more preferably less than 70%, and most preferably less than 60%. In other embodiments, the entire mixture can be aspirated and expelled in the mixing step.

Methods that facilitate gentle mixing include the use of wide-bore pipette tips, slow flow rates and pauses at the end of aspirate and/or expel steps. The term, "cycle" as used herein is defined as a single aspirate/expel step. In the methods of the invention, multiple cycles can be used; that is, liquids can be repeatedly aspirated and expelled from a pipette tip or a pipette tip column.

The lysis step can be carried out for 10 seconds up to 25 minutes. More commonly, the lysis step is performed over a period of between 1 minute to 10 minutes, or 2 minutes to 10 minutes. The preferred duration of lysis is 2 minutes to 5 minutes or most preferably, 3-4 minutes.

Precipitation

The next step is the addition of Precipitation Buffer. Since the method can be performed on an automated workstation, the time at which the Precipitation Buffer is added must be pre-determined. This pre-determined time can be established empirically but must yield a robust and reproducible method.

If alkaline lysis was used, a buffer such as potassium acetate or sodium acetate or an acid is the Precipitation Buffer added at this step to neutralize the mixture. In FIG. 1, the Precipitation Buffer is placed at position 4. In alternate embodiments in which a different lysis procedure was used such as physical lysis, it may not be necessary to neutralize the sample. In preferred embodiments, the Precipitation Buffer may be additionally comprised chaotropic reagents to facilitate capture on a silica resin. A chaotropic agent is a substance which disrupts the three dimensional structure in macromolecules such as proteins, DNA, or RNA and denatures them. Chaotropic agents interfere with stabilizing intramolecular interactions mediated by non-covalent forces such as hydrogen bonds, van der Waals forces, and hydrophobic effects. Examples of chaotropic reagents include urea, thiourea, guanidinium chloride, lithium perchlorate, sodium iodide, sodium perchlorate, guanidine thiocyanate (GuSCN), guanidinium hydrochloride (GuHCl), potassium iodide, potassium chloride, lithium chloride, sodium chloride, urea or mixtures of such substances. In some embodiments, the Precipitation Buffer is comprised of guanidinium HCl and potassium acetate.

Depending on the capacity of the well and the volume of lysed culture in the well, the concentration of guanidinium HCl can be as high as 8M and the potassium acetate concentration can be as high as 3M. Depending on the pH of the mixture containing the lysed cells, the pH of the precipitation buffer can range from about 1 to about 6, preferably between 4 and 6 or more preferably, about 4.5. At this point in the procedure, the pH of the sample should be approximately 4-8 and more preferably, between 4 and 6. Generally reagents of a high concentration are used to limit the volume of the sample as the reagents are added. However, it surprising that the methods of the invention work well because adding concentrated reagents could result in localized regions of concentration distortion, which could negatively impact the process.

Addition of the Precipitation Buffer causes the sample to precipitate or form a sol. A "sol" is defined herein as a colloidal solution that consists of a liquid and a solid. Depending on the sample, the precipitants might float, sink or be suspended throughout the well.

In some embodiments, the neutralization step is separated from the addition of the chaotropic salt. In these embodiments, neutralization can be performed prior to the addition of the chaotropic salts or subsequent.

After addition of the Precipitation Buffer, gentle mixing is performed as described above by repeated aspiration and expulsion of the mixture. In certain embodiments, only a portion of the mixture is aspirated. In these embodiments, the portion aspirated is preferably less than 90%, less than 80%, less than 70%, less than 60%, less than 50% or less than 40% of the total volume of the sample.

The addition, mixing and incubation of the sample with the Precipitation Buffer can be carried out over a period of between 10 seconds and 30 minutes, however, the precipitation step can be performed in 1 minute to 10 minutes, 2 minutes to 10 minutes and preferably, in 5-6 minutes.

Pipette Tip Columns

Next, the plasmid is captured on a pipette tip column. A pipette tip column as defined herein is a column adapted to engage a liquid handler or pipette, either directly or indirectly. In some embodiments the column can be manufactured using a modified pipette tip but it is not necessarily made from a pipette tip. There are no limitations with respect to column shape or materials.

The column contains a solid phase held in place with a bottom frit. In some embodiments, the columns are additionally comprised of a top frit. Non-limiting examples of suitable columns, particularly low dead volume columns include those described in U.S. Pat. No. 7,482,169. It is to be understood that the subject invention is not limited to the use of low dead volume columns. In some embodiments, the columns are configured into plates or racks or used individually.

The solid phase used in the column is preferably a form of water-insoluble particle (e.g., a porous or non-porous bead) that has an affinity for nucleic acids. Silica beads are suitable for the columns of the invention. A non-limiting list of suitable materials includes silicon quartz, celite, diatomaceous earth, silicon carbide, silica gel, (e.g., Davisil, Impaq, Biotage), metal oxides and mixed metal oxides, glass, alumina, zeolites, titanium dioxide and zirconium dioxide and mixtures of these materials.

In alternate embodiments, a different solid phase can be used, such as an ion exchange resin. The ion exchange material may contain either weak base or strong base ion exchange groups. The column may be comprised of organic polymers or an inorganic resin such as silica or other inorganic material. Polymer resins may be agarose, polyvinyl group or other organic groups. Capture conditions are usually from aqueous solution that may contain buffers. Wash conditions could use the same buffers as the capture conditions, but may include different buffers to remove components from the beads that may be held under weaker conditions than the plasmid. Elution conditions will employ changing the pH of the solvent and/or increasing the buffer salt. The pH change will either act on the plasmid to make it less selective for the resin or will act on the ion exchange site to make it less selective for the resin. Ions in the buffer could be added to the eluent to complete for the ion exchange sites and displace the plasmid.

The selectivity of the solid phase for plasmid DNA must be high because the plasmid is captured in the presence of culture medium, cell debris and cell excretions into the medium. These components may compete or interfere with plasmid capture by the columns.

Typically, the column bed size from direct from culture can range from 5 µL to 0.5 mL. In some cases, the bed volume could be as high as 0.6 or 1 mL, provided the column body is large enough to contain the bed and the sample. In general, a smaller bed size will produce higher concentrations of plasmid although the total mass that is recovered may be lower. For 0.1-1 mL cultures, the preferred column bed size ranges from 10 µL to 100 µL. The column bed size used may be increased if the capacity of the resin is lowered and more resin is needed for capture.

The average particle diameter of beads used in the invention is typically in the range of about 20 µm to several hundred micrometers, e.g., diameters in ranges having lower limits of 20 µm, 30 µm, 40 µm, 50 µm, 60 µm, 70 µm, 80 µm, 90 µm, 100 µm, 150 µm, 200 µm, 300 µm, or 500 µm, and upper limits of 10 µm, 20 µm, 30 µm, 40 µm, 50 µm, 60 µm, 70 µm, 80 µm, 90 µm, 100 µm, 150 µm, 200 µm, 300 µm, 500 µm, 750 µm, or 1 mm.

Because the sample contains particulates such as cell debris, it is desirable to use a frit or frits having large pore openings to prevent column clogging. However, increasing the size of frit pore opens requires a corresponding increase in the particle size to prevent the solid phase from falling out of the column. In one embodiment, a single frit (e.g., a lower, or bottom, frit) extends across the open lower end of the column body. In some preferred embodiments of the invention, the bottom frit is located at the open lower end of the column body. This configuration is not required, i.e., in some embodiments, the bottom frit is located at some distance up the column body from the open lower end. Normally, a bed of solid phase medium is positioned inside the open lower end of the column in contact with the bottom frit. The frit should have little or no affinity for nucleic acids.

In certain embodiments, a top frit may be employed. For example, in some embodiments, a second frit or top frit extends across the column between the bottom frit and the open upper end of the column. The position of the top frit can vary; it may just touch the top of the resin bed or it may be positioned substantially above the resin bed.

The performance of the column is typically enhanced by the use of frits having pore or mesh openings sufficiently large to allow cell debris or other particulates to flow through the frit without clogging or plugging under low pressures applied by a pipette or liquid handler. Of course, the pore or mesh openings of course should not be so large that they are unable to adequately contain the extraction media in the chamber. Frits of the invention preferably have pore openings or mesh openings of a size in the range of about 5-500 µm, more preferably 10-200 µm, and still more preferably 100-150 µm, e.g., about 120 µm.

In some cases, it is necessary to consider the relationship between the frit pore size and the particle diameter. Specifically, it is possible to increase the frit pore size when the particle diameter is increased. For example, a frit pore size of 100 µm was used successfully with a range of different resins.

Some embodiments of the invention employ a thin frit, preferably less than 1000 µm in thickness (e.g., in the range of 20-1000 µm, 40-350 µm, or 50-350 µm), more preferably less than 200 µm in thickness (e.g., in the range of 20-200 µm, 40-200 µm, or 50-200 µm), more preferably less than 100 µm in thickness (e.g., in the range of 20-100 µm, 40-100 µm, or 50-100 µm). However, thicker frits, up to several mm, 5 and even 10 mm, thick may be used if the pore size of the frit can be increased dramatically. Increasing the frit thickness can only be done if the pore size is increased.

Some preferred embodiments of the invention employ a membrane screen as the frit. The use of membrane screens as described herein typically provide this low resistance to flow and hence better flow rates, reduced back pressure and minimal distortion of the medium. The membrane can be a woven or non-woven mesh of fibers that may be a mesh weave, a random orientated mat of fibers i.e. a "polymer paper," a spun bonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the sample and various processing liquids through the column bed, may be attached to the column body, is strong enough to withstand the bed packing process, is strong enough to hold the column bed of beads, and does not interfere with the extraction process i.e. does not adsorb or denature the sample molecules.

The frits of the invention can be made from any material that has the required physical properties as described herein. Examples of suitable materials include polymer, sintered polymer, fiber, nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, vinyl polymer, other polymer, metal, ceramic and glass.

In certain embodiments of the invention, a wad of fibrous material is included in the column, which extends across the open channel below the open upper end of the column body, wherein the wad of fibrous material and open channel define a media chamber, wherein the medium is positioned within the media chamber. This wad of fiber can be a porous material of glass, polymer, metal, or other material having large pores. In some embodiments, the wad of fibrous material is used in lieu of an upper frit.

The frit can be attached to the column body by any means which results in a stable attachment. For example, the screen can be bonded to the column body through welding or gluing. The column body can be welded to the frit by melting the body into the frit, or melting the frit into the body, or both. Alternatively, a frit can be attached by a friction fit or by means of an annular pip, as described in U.S. Pat. No. 5,833,927.

Figure 2:
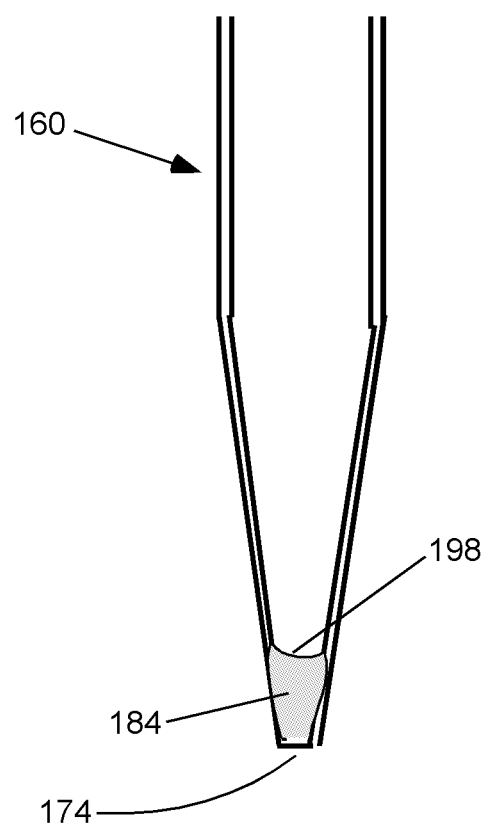
FIG. 2 depicts an embodiment of a pipette tip column.

FIG. 2 depicts an embodiment of pipette tip column construction. Disposable pipette tip 160 is cut approximately ¼ inch from the lower end and frit 174 is welded to the lower end of the tip body. A silica resin 184 was then transferred into the tip. In certain embodiments, upper frit 198 is placed above the resin, e.g., using a friction fit.

Capture

In general, back and forth flow is used to capture the plasmid; however, one-directional flow through the column can be used for the capture mode provided the flow rate is slow enough to allow the plasmid to be captured by the column media. Both back and forth flow and one directional flow can be used for the equilibration, wash and elution steps.

Gravity flow can be used, especially in parallel, to get increased throughput. That is, when plasmid purification is performed on a liquid handling robot, throughput can be increased by utilizing the liquid handling head simply for dispensing solutions to multiple plates. When the capture is performed by back-and-forth flow, the liquid handling head can only process one plate at a time.

To prepare for the capture step, the pipette tip columns are engaged by the robot and equilibrated by aspirating and expelling an Equilibration Buffer (position 8 in FIG. 1) which is preferably an aqueous solution such as a buffer or water. Alternatively, the equilibration buffer can be passed through the columns by vacuum or gravity flow.

Since the method is performed on an automated workstation, the time at which the capture step is performed must be pre-determined and programmed into the method. Therefore it is necessary that each of the column operations has predictable flow and predictable chemical interactions. Predictable flow means that there are not major differences between columns even though the flow varies from column to column. Therefore, the various operations of the automated method are programmed for specific times and duration.

For the capture step, it is preferred to operate the columns by aspirating and expelling through the open lower end of the column. During the aspiration step, it is desirable to aspirate only the liquid containing the plasmid and to minimize aspiration of cell debris or precipitants as those may clog the column. Several strategies can be used during the capture step to minimize capture of solids. First, air can be aspirated into the equilibrated column after equilibration and then expelled after the column is lowered into the sample mixture to dispel solids away from the open lower end of the column. Second, based on the culture and the reagents used, the depth or z-position of the column can be chosen to minimize particulates in the vicinity of the open lower end of the column. For example, when the precipitants float, it is advantageous to position the open lower end of the pipette tip column close to the well bottom. In these embodiments, the open lower end of the pipette tip column can be positioned just above the well bottom, 1 mm above the well bottom, 2 mm above the well bottom, 3 mm above the well bottom, 4 mm above the well bottom or more. Third, to avoid aspirating particulates, only a portion of the sample can be aspirated into the pipette tip column. The portion aspirated is preferably less than 90%, less than 80%, less than 70%, less than 60%, less than 50% or less than 40% of the total volume of the sample. In some embodiments, the entire sample is aspirated into the pipette tip columns.

The flow rates used in the capture step range from 0.05 mL/min to 3 mL/min. Slower flow rates are generally better than high flow rates because the risk of plugging of the columns is reduced. Slower flow rates will increase the residence time of the liquid interaction of the column, but in some cases only a portion of the sample volume is processed by the column with one flow cycle. In this case, several flow cycles are performed to increase interaction of the column with the sample. Preferred flow rates are 0.1-2 mL/min, 0.2-1 mL/min, and 0.25-0.5 mL/min.

Several approaches can also be used to aid in effective plasmid capture. The flow rate used during the capture step can be relatively slow. For example, the flow rate can be less than 1 ml/min, less than 0.5 ml/min, less than 0.25 ml/min or even less. A pause at the end of each aspirate and/or expel step can also be used to aid in efficient capture. The pause step can be at least 5 seconds, at least 10 seconds, at least 15 seconds, at least 20 seconds, or more. The number of aspirate and expel steps (cycles) can also be increased to facilitate capture. The capture step can be performed using at least 5, at least 10, at least 15, at least 20, at least 25, or even more than 30 cycles.

Wash and Elution

After the capture step, the columns can be moved to a blotting station (FIG. 1, deck position 13) and touched to a Kimwipe or adsorbent one or more times to remove any particulates or cell debris from the open lower end of the columns.

Next, the columns are usually washed one or more times to remove material that is not specifically bound to the solid phase. However in certain embodiments, the wash steps can be omitted. The Wash Buffer is typically comprised of an aqueous solution and an alcohol such as ethanol or 2-propanol. For example, in some embodiments, the Wash Buffer is comprised Tris-HCl buffer and ethanol. In these embodiments the concentration of the Tris-HCl buffer can be in the range of 10 mM to 10 M with the pH ranging from 4 to 12 and the ethanol concentration can range from 40-95%. When more than one wash is performed, the same wash solution can be used for multiple washes or different wash solutions can be used. In FIG. 1, three wash stations are depicted at positions 7, 10 and 11.

Wash steps can be performed with back and forth flow or unidirectional flow using gravity or vacuum. The advantage of performing the wash steps by unidirectional flow is that higher throughput can be achieved. That is, when plasmid purification is performed on a liquid handling robot, throughput can be increased by utilizing the liquid handling head simply for dispensing wash solution to multiple plates. When the wash is performed by back-and-forth flow, the liquid handling head can only process one plate at a time.

After the wash step, air is passed through the columns to remove any organic solvent remaining from the wash step. This can be accomplished by depositing the pipette tip columns onto a vacuum block (FIG. 1, Vacuum Station) and drawing air through the columns with a vacuum. A vacuum block adaptor was custom built for this process and is described in more detail below.

In certain embodiments, air is passed through the columns long enough to remove the organic solvent present in the wash solution, but not long enough to dry the columns completely. When the residual organic solvent is measured, it is in the range of less than 10%, less than 9%, less than 8%, less than 7%, less than 6%, less than 5%, less than 4%, less than 3%, less than 2% or less than 1%.

In other embodiments, the columns can be dried completely. Complete drying is not preferred, but only because it requires more time. However, if the pump is sufficiently strong, the columns can be dried completely without sacrificing significant time.

In still other embodiments, air is passed through the columns with positive pressure. Alternatively, it is possible to dry or remove the ethanol or other organic solvent after elution by methods such as speed-vac, air drying, heating or applying a gas stream to the wells containing the eluted sample.

The elution of plasmid from the column can be accomplished with back and forth flow or one direction flow. Generally elution volumes are in the range of about 1-5 times the bed volume however; elution volumes can range from 0.25 to 10 times the column bed volume, preferably in the range of 1-5 times the bed volume, and more preferably 3 times the bed volume. Multiple elution volumes can be used to elute all of the material off of the column.

When back-and-forth flow is used, air can be aspirated into the pipette tip column prior to aspirating the elution buffer. This air can be used after the plasmid is expelled from the column to ensure complete expulsion of all the liquid in the column.

Generally, the Elution Buffer is aqueous and has a pH between 6 and 10. In some embodiments, the column is incubated with the elution buffer for a period of time. In these embodiments, the column and elution buffer are incubated for at least 1 minute, at least 2 minutes, at least 3 minutes, at least 4 minutes, at least 5 minutes, at least 10 minutes or at least 15 minutes. In other embodiments, the incubation step is omitted.

After the incubation step, the purified plasmid is expelled from the pipette tip column. To ensure the maximum volume of purified plasmid is recovered, a blow-out step can be performed by expelling the air aspirated as described above.

The concentration of plasmid DNA purified by this method is generally in the range of 5 ng/uL to 250 ng/uL, and more commonly in the range of 10-100 ng/mL. The amount of plasmid DNA obtained is in the range of 0.1-30 µg, 0.2-20 µg and 1-10 mg. The $A_{260/280}$ ratio from the purified plasmid is between 1.8 and 2.0. Most importantly, the plasmid DNA purified by these methods is high quality and can be used for any downstream application including sequencing, transfection and transformation.

For a given culture, plasmid yield and concentration depend on (1) elution volume, (2) resin bed size, and (3) starting culture volume. Smaller elution volumes increase concentration. Smaller bed sizes increase concentrations but reduce yield because they have less capacity. Larger culture volumes can increase both concentration and yield.

For example, an 80-uL resin bed and a 100-uL elution volume yields 1-3 µg of plasmid DNA with a concentration of 20-40 ng/µL from 150 µL of a 16-hour culture. If the elution volume used is halved or decreased to 50 µL the yield would be expected to either stay same or decrease slightly from 1-3 µg but the concentration would be expected to increase to 40-80 ng/µL. If the resin bed size is decreased to 40 or 20 µL with 100 µL elution volume, both the yield and concentration will either stay same or decrease slightly. In another example, if the resin bed size is decreased to 40 or 20 µL resin bed but eluted with 50 µL elution volume, the yield will stay either same or decrease slightly but the concentration will increase by factor of two. In another example, from 300 µL of 16-hour grown culture, 3-7 µg of plasmid DNA can be purified with 30-70 ng/µL concentration when eluted with 100 µL. When resin bed volume and elution volumes change, similar results are obtained as described above with 150 µL culture volume examples. If the starting culture volume is increased, the yield and concentration will increase proportionately. If sufficient growth is achieved the yield and concentrations will generally increase proportionally as the culture volumes increase to 1 mL, 2 mL and 3 mL or more.

Volume Constraints Imposed by the Microplate Format

Since the methods of the invention can be automated in a 96-well format, one of the greatest challenges overcome by the invention is the volume constraint imposed by the use of a 96-well microplate. Several solutions (RNase, Lysis Buffer and Precipitation Buffer) are added to the sample prior to capture on the column however, each well can hold only a very limited volume. Generally, the maximum volume available in a 96-well deep well plate is 2.2 mL. Although plates having 4-mL wells exist, they are not commonly used and may not be compatible with some robotic liquid handlers. The volume of bacterial culture that can be used depends in part on the total volume of the well and partly on the volumes of the Lysis and Precipitation Buffers that will be added to the culture. The total volume cannot exceed the volume of the well in which the mixture is contained. In addition to the mixture volume, there is also the volume of liquid displaced when the column is inserted into the mixture to process the sample. However, this volume is relatively small and is not considered in the calculations described below in Tables 1 and 2.

In 96-well plates, the well capacity can be 0.2, 0.5, 1.0, 1.5, 2.0 or 2.2 mL. It may also be possible to use 4-mL deep-well plates, in which case the volumes listed below could be doubled. Other plate formats could also be used with the invention such as 6, 12, 24, 48, 72 or 384-well plates. For individual tubes, a common volume is 1.7 mL although tubes up to approximately 5 mL can also be used in parallel.

Table 1 shows increasing volumes of culture, ranging from 0.1 mL to 1.0 mL. With the concentration of the Lysis and Precipitation Buffers listed in the examples below, the total volume of solution per well ranges from 0.34 mL to 3.4 mL.

TABLE 1

Plasmid capture with less concentrated starting buffers

| | Starting concentrate | Working concentration |
|---|---|---|
| Lysis Buffer | 0.2M NaOH<br>2.5% SDS[1] | 0.1M NaOH<br>1.25% SDS |
| Precipitation Buffer | 4.2M Guanidinium HCl<br>0.9M KOAc[2] pH 4.5 | 1.72M Guanidinium HCl<br>0.37M KOAc pH 4.5 |

| | | | | | | | |
|---|---|---|---|---|---|---|---|
| Starting culture volume (µL) | 100 | 150 | 300 | 450 | 600 | 900 | 1000 |
| Lysis Buffer (µL) | 100 | 150 | 300 | 450 | 600 | 900 | 1000 |
| Precipitation Buffer (µL) | 140 | 210 | 420 | 630 | 840 | 1050 | 1400 |
| Total Volume prior to capture (µL) | 340 | 510 | 1020 | 1530 | 2040 | 2850 | 3400 |

[1]SDS is sodium dodecylsulfate
[2]KOAc is potassium acetate

However, when more concentrated Lysis and Precipitation Buffers are used, as illustrated in Table 2, it is possible to start with 1 mL of culture and the maximum volume of liquid per well is 2.2 mL. This means that larger culture volumes could be used: approximately 1.8 mL of culture if a 4 mL plate were used.

Even more concentrated Lysis Buffers could be used allowing even larger volumes of culture sample It is possible to use up to 10% concentrated SDS and up to 17.6 M NaOH. The use of guanidinium thiocyanate (SCN) in the Precipitation Buffer could increase the possible concentration of this solution up to 6-8 M because of increased solubility. The SCN is a more effective chaotropic reagent and could be buffered to the appropriate pH. With the use of more concentrated buffers up to 3-3.3 mL of culture could be grown in a 4-ml well, if sufficient aeration is achieved for cell growth.

It should also be noted that significant evaporation occurs during cell growth. For example, after 16 hours of growth at 37° C., a well containing 220 μL had only 150 μL and a well containing 370 μL had only 300 μL.

TABLE 2

Plasmid capture with more concentrated starting buffers

| | Starting concentrate | Working concentration |
|---|---|---|
| Lysis Buffer | 0.3M NaOH<br>3.7% SDS | 0.1M NaOH*<br>1.25% SDS* |
| Precipitation Buffer | 4.8M Guanidinium HCl<br>1.16M KOAc pH 4.5 | 1.5M Guanidinium HCl*<br>0.37M KOAc pH 4.5* |

| | | | | | | | |
|---|---|---|---|---|---|---|---|
| Starting culture volume (μL) | 100 | 150 | 300 | 450 | 600 | 900 | 1000 |
| Lysis Buffer (μL) | 50 | 75 | 150 | 225 | 300 | 450 | 500 |
| Precipitation Buffer (μL) | 70 | 105 | 210 | 315 | 420 | 630 | 700 |
| Total Volume prior to capture (μL) | 220 | 330 | 660 | 990 | 1320 | 1980 | 2200 |

*calculated based on 300 uL of culture, 150 uL concentrated Lysis Buffer and 210 uL concentrated Precipitation Buffer All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Evaluation of an 80 μL Bed Volume Pipette Tip Column Containing a Silica Resin for Purification of Plasmid from Eukaryotic Cells In this example, the performance of 80 μL bed volume pipette tip columns is evaluated. The pipette tip column is constructed from a 500 μL pipette tip (Tecan) and is packed with a silica-based particle resin. These columns, buffer conditions and column processing procedures are tested for the recovery of DNA plasmids from complicated samples. The yield and quality are assessed by UV spectrometry and agarose gel electrophoresis.

Samples are prepared by first growing a single yeast colony in 25 mL media supplemented with the appropriate carbon source and antibiotic to propagate cells containing the DNA vector. The liquid culture is incubated at 30° C. with shaking until the media becomes turbid. The culture is divided into equal aliquots.

To purify the DNA plasmids from the lysed yeast cells, the pipette tip columns are processed by the ME semi-automated purification system (PhyNexus, Inc.). The columns are equilibrated with 200 μL 7M guanidinium-HCl by performing one cycle of back-and-forth flow at 500 μL/min and 20 second pauses at the end of each aspirate and each dispense step. One cycle of back-and-forth flow consists of aspirating and expelling the solution through the lower end of the pipette tip column.

The yeast culture is subjected to RNase and lysis and with a base/detergent mixture and processing with a pipette tip by using at least 24 back-and-forth cycles of 250 μL/min and 20 second pauses after the end of each aspirate and dispense step.

The lysed culture is precipitated by adding neutral buffer and guanidinium-HCl and by using at least 24 back-and-forth cycles of 250 μL/min and 20 second pauses after the end of each aspirate and dispense step.

The pipette tip column processing for capture of the plasmid DNA is done using at least 24 back-and-forth cycles at a flow rate of 250 μL/min with 20 second pauses after the end of each aspirate and dispense step.

Following plasmid capture on the pipette tip column, the columns are washed with 200 μL Wash 1 Buffer consisting of 10 mM Tris-HCl pH 6.6, 5M guanidinium-HCl and 30% ethanol. This is followed by a second wash in Wash 2 Buffer consisting of 10 mM Tris-HCl pH 7.5 and 80% ethanol. Both wash procedures proceed by one cycle of back-and-forth flow at 500 μL/min and 20 second pauses at the end of each aspirate and expel step. A blow out step is performed after the washes to remove all residual Wash Buffer from the resin bed.

DNA plasmid is released from the column with 300 μL Elution Solution consisting of water. The procedure to release the DNA is 8 back-and-forth cycles at 250 μL/min with 20 second pauses after the end of each aspirate and dispense step.

DNA is quantified by absorbance at 260 nm. The quality of the DNA is assessed by the shape of the absorbance spectrum, the ratio of absorbance at 260 nm to the absorbance at 280 nm, agarose gel electrophoresis and transformation efficiency. No RNA or genomic DNA is observed on the agarose gel.

Example 2

Purification of Plasmid DNA from *E. coli* Using the PhyNexus ME or MEA

Columns and methods for purifying plasmids DNA from *E. coli* lysate were developed for 12 at-a-time sample format. The method was designed to operate on a PhyNexus ME and MEA Personal Purification Instruments and other robotic liquid handlers. The procedure used was as follows.

1. Add 150 μL of Lysis Buffer containing RNase to 350 μL of cell culture containing plasmid. Mix using gentle pipette mixing with wide bore 1000 μL pipette tips for 30 back-and-forth cycles of 1 mL/min. On the final dispense, blow-out an extra 2 μL. Wait 5 minutes.

2. Add 210 µL of Precipitation Buffer to lysed cells using gentle pipette mixing with 1000 µL pipette tips for 8 back-and-forth cycles of 1.2 mL/min. On the final dispense, blow out an extra 2 µL.
3. Discard pipette tips and attach plasmid DNA pipette tip columns to 12-channel head.
4. Setup a 96-well microplate consisting of 1 mL, pyramid-bottom wells with 1 row of 300 µL Equilibration Buffer, 1 row of 500 µL Wash 1 Buffer, 2 rows of 500 µL Wash 2 Buffer, 1 row of 130 µL Elution Solution and 1 row of 120 µL Elution Solution.
5. Equilibrate the pipette tip columns by cycling 180 µL Equilibration Buffer back-and forth through the column twice using a flow rate of 0.5 mL/min and a 20 second pause at the end of each aspirate and each expel step.
6. Move the pipette tip columns out of the Equilibration Buffer and intake 100 µL of air at a flow rate of 0.25 mL/min.
7. Lower the pipette tip columns into the prepared cell lysate and blowout 100 µL at a flow rate of 1 mL/min and pause 5 seconds.
8. Capture the plasmid DNA by cycling 180 µL of the plasmid preparation from step 2 back-and-forth 14 times at flow rate of 0.25 mL/min and 20 second pauses at the end of each aspirate and each expel step.
9. Wash the pipette tip columns in Wash 1 Buffer by cycling 180 µL back-and-forth 2 times at flow rate of 0.5 mL/min and 20 second pauses at the end of each aspirate and each expel step.
10. Wash the pipette tip columns in Wash 2 Buffer by cycling 180 µL back-and-forth 4 times at flow rate of 0.5 mL/min and 20 second pauses at the end of each aspirate and each expel step.
11. Wash the pipette tip columns in Wash 2 Buffer by cycling 180 µL back-and-forth 2 times at flow rate of 0.5 mL/min and 20 second pauses at the end of each aspirate and each expel step.
12. Transfer pipette tip columns to drying block and apply vacuum to dry ethanol. Use a vacuum capable of 6 cubic feet per minute of flow to dry the columns for 5 minutes.
13. Elute the captured plasmid DNA by aspirating 150 µL of Elution Solution at a flow rate of 0.5 mL/minute and pause for 5 minutes to incubate. Dispense 150 µL at a flow rate of 1 mL/min.
14. Perform the second elution by aspirating 120 µL of Elution Solution at a flow rate of 0.5 mL/minute and pause for 5 minutes to incubate. Dispense 120 µL at a flow rate of 1 mL/min.

The columns used in this example were 80 µL bed columns fitted with 100 µm pore size screen bottom frits. Columns were packed either with or without a top screen frit of 100 µm pore size. The top frit was fitted approximately 15-20 mm above the column bed. Columns contained several types of silica resin.

Overnight E. coli cultures containing 1.4 mL in a 96 deep well plate were used as samples.
Buffers
Resuspension Buffer: 50 mM Tris-HCl pH 8.0, 10 mM EDTA, 100 ug/mL RNase A
Lysis Buffer: 200 mM NaOH, 1% SDS
Precipitation Buffer: 4.2 M guanidine hydrochloride, 0.9M Potassium acetate pH 4.8
Equilibration Buffer: 7M Gu-HCl pH 5.5
Wash 1 Buffer: 5M guanidine HCl, 30% Ethanol, 10 mM TRIS-HCl pH 6.6
Wash 2 Buffer: 10 mM TRIS-HCl pH 7.5, 80% Ethanol
Elution Solution: Water The yield ranged from 1 µg to 5 µg per well. The plasmid DNA was transformation/transfection quality with no RNA contamination. The purity was examined with slab gel electrophoresis and UV absorption with A260/A280 ratio between 1.8 and 2.0. No RNA or genomic DNA was observed on the agarose gel.

Example 3

Plasmid Purification from 150 µL E. coli Cultures

Columns and methods for purifying plasmid DNA from E. coli were developed for 96 at-a-time sample format. The method was designed to operate on a Tecan Freedom Evo® or other robotic liquid handlers. The columns used in this example were 80 µL bed columns containing silica resin and fitted with 100 µm pore size screen bottom frits. Columns were packed with or without a top screen frit of 100 µm pore size. The top frit was positioned either a fraction of a mm or several mm above the column bed. The procedure used was as follows.
Growth of E. coli Liquid Cultures Three different growth media were evaluated. A test tube containing 5 mL Luria Broth (PML Microbiologicals, Cat. #B8474) culture, supplemented with ampicillin to a final concentration of 100 µg/mL was inoculated with a single colony of DH5α harboring a pCR2.1-TOPO cloning vector (Invitrogen, Cat. #K4560-01) grown on an LB agar Petri dish supplemented with ampicillin to a final concentration of 100 µg/mL). The culture was grown for 16 hours at 37° C. with shaking at 300 RPM using a shaking incubator (New Brunswick Labs).

To evaluate the performance of different growth media, 10 mL Luria Broth, EnPresso (BioSilta), or Agencourt Ale Bacterial Growth Media (Beckman, Cat. #A29211) were each supplemented with ampicillin to a final concentration of 100 µg/mL. These were subsequently inoculated with 10 µL the overnight culture described above. 150 µL of these freshly inoculated cultures was transferred to a 96-well, V-bottom microplate consisting of 250 µL wells (Corning, Cat. #3363) or a 96-well, V-bottom storage plate consisting of 1.1 mL wells (Seahorse Biosciences, Cat. #S30026). After 16 hours, all cultures became turbid indicating growth of plasmid-carrying bacterial cells.
Cell Harvest Two plasmid purification procedures were compared. Plasmids were either purified directly from the 150 µL cell culture or cells were harvested from the 150 µL cell culture, first, in order to remove the growth media. To harvest cells, cultures were collected into microcentrifuge tubes. These tubes were centrifuged at 10,000 RPM for 10 minutes using a microcentrifuge. Supernatant was removed from the pelleted cells. Pelleted cells from the 150 µL cultures were resuspended in 150 µL of Resuspension Buffer.
Plasmid Purification
1. Purification of plasmids from 150 µL cultures proceeded as follows. 150 µL of Lysis Buffer containing RNase was added directly to cell cultures or to resuspended pellets using the Tecan Freedom Evo® liquid handling robot. This was followed by 8 cycles of mixing at a flow rate of 8 µL/sec. The robot next added 210 µL Precipitation Buffer and the samples were mixed with 8 cycles at a flow rate of 8 µL/sec. These samples were processed by pipette tip columns using the Tecan Freedom Evo®.
2. Setup four, 96-well microplates (2 mL, pyramid-bottom wells), one with each solution as follows. 300 µL Equilibration Buffer, 500 μL Wash 1 Buffer, 500 μL Wash 2 Buffer, and 130 μL Elution Solution.
3. Equilibrate the pipette tip columns by cycling 180 μL Equilibration Buffer back-and forth through the column twice using a flow rate of 0.5 mL/min and a 20 second pause at the end of each aspirate and each expel step.
4. Move the pipette tip columns out of the Equilibration Buffer and intake 100 μL of air at a flow rate of 0.25 mL/min.
5. Lower the pipette tip columns into the cell lysate prepared in step 1 and blowout 100 μL at a flow rate of 10 mL/min and pause 5 seconds.
6. Capture the plasmid DNA by cycling 180 μL back-and-forth 14 times at flow rate of 0.25 mL/min and 20 second pauses at the ends of each aspirate and each expel steps.
7. Wash the pipette tip columns in Wash 1 Buffer by cycling 180 μL back-and-forth 2 times at flow rate of 0.5 mL/min and 20 second pauses at the end of each aspirate and each expel step.
8. Wash the pipette tip columns in Wash 2 Buffer by cycling 180 μL back-and-forth 4 times at flow rate of 0.5 mL/min and 20 second pauses at the end of each aspirate and each expel step.
9. Wash the pipette tip columns in Wash 2 Buffer by cycling 180 μL back-and-forth 2 times at flow rate of 0.5 mL/min and 20 second pauses at the end of each aspirate and each expel step. Optionally additional washes are performed. Optionally additional wash buffers are used.
10. Transfer pipette tip columns to drying block and apply vacuum to dry ethanol. Use a vacuum capable of 6 cubic feet per minute of flow, dry the columns for 5 minutes.
11. Elute the captured plasmid DNA by aspirating 150 μL of water at a flow rate of 0.5 mL/minute and pause for 5 minutes to incubate. Dispense 150 μL at a flow rate of 10 mL/min.
12. Perform the second elution by aspirating 120 μL of water at a flow rate of 0.5 mL/minute and pause for 5 minutes to incubate. Dispense 120 μL at a flow rate of 10 mL/min.

Results

The cells grew to different densities in the three different media as measured by light scattering at 600 nm using the NanoDrop UV spectrometer. Luria broth grew cultures to relatively the same density in all 4 cultures. Agencourt grew cells to a slightly higher density in 3 cultures with 1 culture grown to a low density. Three EnPresso cultures grew to the highest density with one culture grown to a low density. There was little difference in yield from pellets or from cell culture.

The yield was greater than 3 μg per well and was transformation/transfection quality DNA with no RNA contamination. The purity was examined with slab gel electrophoresis and UV absorption with A260/A280 ratio between 1.6 and 2.0. No RNA or genomic DNA was observed on the agarose gel.

Example 4

Plasmid Purification from 350 μL E. coli Cultures

Columns and methods for purifying plasmid DNA from E. coli were developed for 96 at-a-time sample format. The method was designed to operate on a Tecan Freedom Evo® or other robotic liquid handlers. The procedure was as follows.

E. coli Liquid Cultures

Cultures were grown as described in Example 3. Three different growth media were evaluated, Luria Broth (PML Microbiologicals, Cat. #B8474), EnPresso (BioSilta), or Agencourt Ale Bacterial Growth Media (Beckman, Cat. #A29211). 350 μL of freshly inoculated culture was transferred to a 96-well, V-bottom microplate consisting of 1.1 mL wells (Seahorse Biosciences, Cat. #S30026). Cells were grown by shaking at 300 RPM at 37° C. for 16 hours. After 16 hours, all cultures became turbid, indicating growth of plasmid-carrying bacterial cells.

Cell Harvest

Two plasmid purification procedures were tested. Plasmids were either purified directly from the 350 μL cell culture or cells were harvested from the 350 μL cell culture first, in order to remove growth media. To harvest cells, cultures were collected into microcentrifuge tubes. These tubes were centrifuged at 10,000 RPM for 10 minutes using a microcentrifuge. The supernatant was removed from the pelleted cells. Pelleted cells from the 350 μL cultures were resuspended in 350 μL of Resuspension Buffer.

Plasmid Purification

Purification of plasmids from 350 μL cultures proceeded as follows. 350 μL of Lysis Buffer was added directly to cell cultures or to resuspended pellets using the Tecan Freedom Evo® liquid handling robot. This was followed by 8 cycles of mixing at a flow rate of 8 μL/sec. The robot next added 480 μL Precipitation Buffer and the samples were mixed with 8 cycles at a flow rate of 8 μL/sec. These samples were processed pipette tip columns using the Tecan Freedom Evo® as described in Example 3.

The pipette tip columns used in this example were 80 μL bed columns fitted with 100 μm pore size screen bottom frits. Columns were packed with and without a top screen frit of 100 μm pore size. The top frit was fitted approximately 15-20 mm above the column bed. The columns contained silica resin.

Results

The three different media grew cells to different densities as measured by light scattering at 600 nm using the NanoDrop UV spectrometer. Luria broth grew cultures to relatively the same density in all 4 cultures. The EnPresso cultures consistently grew to a higher density. The Agencourt medium grew cells to the highest density. Compared to the 150 μL cultures grown in Example 3, the 350 μL cultures grew to a lower density. Nevertheless, because the starting volume was larger in the 350 μL culture, the plasmid yield was greater than that obtained from the 150 μL culture.

TABLE 2

Plasmid Purification from 350 μL bacterial cultures

| Sample Name | $A_{600}$ | Culture Vol. (μL) | Purification Method | $A_{260}$ | $A_{260}/A_{280}$ | Conc. (ng/μL) | Vol. (μL) | Total (μg) |
|---|---|---|---|---|---|---|---|---|
| Luria Broth - from culture | 0.386 | 350 | pipette tip Column | 0.090 | 2.4 | 4.4 | 100.0 | 0.4 |
| Luria Broth - from pellet | 0.394 | 350 | pipette tip Column | 0.080 | 3.0 | 4.2 | 100.0 | 0.4 |
| EnPresso - from culture | 0.420 | 350 | pipette tip Column | 0.130 | 2.0 | 6.3 | 100.0 | 0.6 |
| EnPresso - from pellet | 0.514 | 350 | pipette tip Column | 0.110 | 2.0 | 5.4 | 100.0 | 0.5 |

TABLE 2-continued

Plasmid Purification from 350 µL bacterial cultures

| Sample Name | $A_{600}$ | Culture Vol. (µL) | Purification Method | $A_{260}$ | $A_{260}/A_{280}$ | Conc. (ng/µL) | Vol. (µL) | Total (µg) |
|---|---|---|---|---|---|---|---|---|
| Agencourt - from culture | 0.760 | 350 | pipette tip Column | 0.330 | 1.9 | 16.5 | 100.0 | 1.7 |
| Agencourt - from pellet | 0.782 | 350 | pipette tip Column | 0.130 | 3.0 | 6.1 | 100.0 | 0.6 |

Example 5

Plasmid Purification from 1 mL *E. coli* Cultures

Columns and methods for purifying plasmid DNA from *E. coli* are developed for a 96 at-a-time format. The method is designed to operate on a Tecan Freedom Evo®, Dynamic Devices Oasis® or other robotic liquid handlers. The procedure used is as follows.

Growth of *E. coli* Liquid Cultures

Two different growth media are evaluated, Luria Broth (PML Microbiologicals, Cat. #B8474) or EnPresso (Bio-Silta). 1 mL of each media is supplemented with ampicillin to a final concentration of 80 µg/mL and inoculated with a single colony of *E. coli* strain DH5α harboring a TOPO vector from an LB agar plate supplemented with ampicillin. The culture is divided into 150 µL aliquots and transferred to separate wells of a 2 mL deep-well, round bottom plate. The plate is covered with a gas permeable membrane. The cultures are incubated at 37° C. with orbital shaking at 300 rpm for 16 hours. After 16 hours, all cultures are turbid indicating growth of plasmid-carrying bacterial cells.

Cell Harvest

To harvest cells, 1 mL of each of the culture is collected into microcentrifuge tubes. These tubes are centrifuged at 10,000 RPM for 10 minutes using a microcentrifuge. The supernatant is removed from the pelleted cells and the pelleted cells are resuspended in 150 µL of Resuspension Buffer.

Plasmid Purification

Purification of plasmids from the resuspended cells proceeds as follows. 150 µL of Lysis Buffer is added to resuspended pellets using the liquid handling robot. This is followed by 8 cycles of mixing. The robot next adds 210 µL Precipitation Buffer and the samples are mixed with 8 cycles.

These samples are processed by 1 mL body pipette tip columns. The pipette tip columns used in this example are 80 µL bed columns fitted with 120 µm pore size screen bottom frits. Columns are packed with silica resin, either with or without a top screen frit of 100 µm pore size.

Results

The cells grow to different densities in the three different media as measured by light scattering at 600 nm using the NanoDrop UV spectrometer. The grow to relatively low density in Luria Broth and higher densities in the EnPresso and Agencourt Ale. In this example, yield of plasmid from EnPresso and Agencourt media is comparable. The yield is greater than 3 mg per well. The purity is examined with slab gel electrophoresis and UV absorption with A260/A280 ratio between 1.6 and 2.0. No RNA or genomic DNA is observed on the agarose gel.

Example 6

Plasmid Purification from 0.150 mL *E. coli* Cultures and Genomic DNA Removal

Columns and methods for purifying plasmid DNA from *E. coli* are developed for 96 at a time sample format. The method is designed to operate on a PhyNexus MEA personal purification instrument or other robotic liquid handlers. The procedure is as follows.

Growth of cells and purification are performed as described above except with modifications to the precipitation procedure. To address the genomic DNA contamination, the precipitation step is modified. After the lysis step, the genomic DNA is released into the solution. This genomic DNA must be precipitated from the sample in order to selectively capture the plasmid DNA without interference or contamination from the genomic DNA.

The two-step precipitation procedure consists of adding 94.7 µL 5 M potassium acetate pH 5.7 to the lysed sample first, before the addition of the chaotropic salt. The potassium acetate is mixed using the MEA and wide bore tips to perform 2 mix cycles at the bottom, middle and 5 mm beneath the top of the sample. A mix cycle consists of 180 µL aspirate and dispense at 6 mL/min and 2 second pauses at the end of each aspirate and dispense step. Next, 263.82 µL 8 M guanidine-HCl is added to the sample. 4 cycles of mixing at the bottom, 3 cycles in the middle and 3 cycles at 5 mm beneath the top of the sample is used to fully precipitate the sample. Pipette tip columns are used to purify the plasmid.

Results

In this experiment, the samples are precipitated in two steps in order to improve precipitation. The quantity of nucleic acid is monitored by UV absorbance and agarose gel electrophoresis is used to determine the purity of the sample. The yield was up 1-10 µg per well and was sequencing quality. Transformation/transfection quality DNA may also be obtained with no RNA contamination. The purity was examined with slab gel electrophoresis and UV absorption with A260/A280 ratio between 1.6 and 2.0.

Example 7

Fully Automated 96 Sample Prep Method on Robotic Platform

A Beckman Biomek FX robotic liquid handler is set up for 96 at a time processing of samples according to the drawing in FIG. 1.

Deck position 0: pipette column Adaptor [Cat.#: DAB 96-000-01(Beckman)] with pipette columns
Deck position 1: Regular pipette tips for RNase A
Deck position 2: Wide bore pipette tips for Lysis
Deck position 3: Wide bore pipette tips for Precipitation
Deck position 4: Reservoir with 15 mL Precipitation Buffer (PB(p))
Deck position 5: Reservoir with 15 mL Lysis Buffer (LB(p))
Deck position 6: Reservoir with 2 mL RNase A
Deck position 7: Deep well plate [Cat.#: PCP 96-20-10] containing 500 µL of Wash Buffer in each well (WB(p))
Deck position 8: Deep well plate [Cat.#: PCP 96-20-10] containing 500 µL of de-ionized water in each well
Deck position 9: Deep well plate overnight culture Deck position 10: Deep well plate [Cat.#: PCP 96-20-10] containing 500 μL of Wash Buffer in each well (WB(p))

Deck position 11: Deep well plate [Cat.#: PCP 96-20-10] containing 500 μL of Wash Buffer in each well (WB(p))

Deck position 12: 250 μL elution plate [Cat.#: PCP 90-00-10] containing 130 μL of Elution (EB(p))

Deck position 13: Kimwipes attaches to upside down lid of tip box for blotting

Deck position 14: (Optional) 250 μL plate [Cat.#: PCP 90-00-10] containing 120 μL of buffer in each well for second the elution The positioning of the various plates is shown for illustrative purposes only. Various plates, solutions, solution types and volumes can be positioned in any combination of plate positions. Other robotic liquid handlers can use different layouts.

The following procedure is used to grow and process the samples.

1) Transfer (Method A) 220 μL or (Method B) 370 μL of growth media containing appropriate selective agent to each well of a 96-well, deep well plate.
2) Inoculate each a single bacterial colony from a fresh plate.
3) Cover the plate with a gas permeable seal and shake at 300 rpm at 37° C. for 16 hours.

After 16 hours of growth, ~70 μL evaporates. (Method A) will be left with 150 μL while (Method B) will be left with 300 μL.

4) Transfer pipette columns from shipped box to Adaptor for pipette columns [Cat.#: DAB 96-000-01(Beckman)]. For ease of transferring 96 pipette columns, transfer tools are available [Cat.#: DAB 12-000-02 (Beckman)]. Place the adaptor with pipette columns on the deck position 0.

On the robotic instrument set up the deck as described above.

5) Place the deep well block on deck position 9.
6) Using regular pipette tips from deck position 1, transfer (Method A) 6 μL or (Method B) 12 μL of RNase A from deck position 2 to the cell culture at deck position 9.
7) Using wide bore pipette tips from deck position 2, transfer (Method A) 150 μL or (Method B) 300 μL of lysis buffer from deck position 5 to the cell culture at deck position 9.
8) Lyse the cells using 8 mix steps of 180 μL at a flow rate of 2 mL/min flow rate with 2 second pauses after each aspirate and each dispense step. Discard the tips.
9) Using wide bore pipette tips from deck position 3, transfer (Method A) 210 μL or (Method B) 420 μL of precipitation buffer from deck position 4 to the lysed cells at deck position 9.
10) Precipitate the lysed cells using 8 mix steps 190 μL at a flow rate of 2 mL/min flow rate with 2 second pauses after each aspirate and each dispense step. Discard the tips.
11) Engage pipette columns from deck position 0. Make sure to define the pipette columns as a new consumable. The pipette columns have the same length as the regular 200 μL tips and therefore do not need to change tip heights for pipette tip columns.
12) Equilibrate pipette columns with 2 mix steps of 170 μL equilibration buffer (deck position 8) using a flow rate of 0.78 ml/min with 5 second pause at the end of each aspirate and each dispense step.
13) Move pipette columns out of the equilibration buffer and aspirate 180 μL of air at 0.25 ml/min flow rate with 2 second pause.
14) Lower the pipette columns to the lysed, precipitated sample (deck position 9) 1 mm from the bottom of the wells. Dispense 170 μL of air at 0.25 ml/min flow rate with 2 second.
15) Maintain the pipette columns at 1 mm above the bottom of the well. Capture the plasmid DNA using 12 mix steps (Method A) or 20 mix steps (Method B) of 180 μL at a flow rate of 0.25 ml/min with 10-20 second pauses at the end of each aspirate and each dispense step.

*Make sure that the pipette tip columns do not come up (in Z direction) and stay at same position after step 14.

16) After capture step, move pipette tip columns over the blotting station (deck position 13). Move pipette columns down in the Z-direction to touch the Kimwipes on the blotting station to remove cell debris from the columns. Repeat once.
17) Move pipette columns into wash buffer (deck position 7). Wash the captured plasmid DNA with 2 cycles at 2 mL/min flow rate with 10 second pause.
18) Move pipette columns into wash buffer (deck position 10). Wash the captured plasmid DNA with 2 cycles at 2 mL/min flow rate with 10 second pause.
19) Move pipette columns into wash buffer (deck position 11). Wash the captured plasmid DNA with 2 cycles at 2 mL/min flow rate with 10 second pause.
20) Eject the pipette columns back into the column adaptor (deck position 0).
21) Move the adaptor carrying the pipette tip columns to the vacuum drying station and apply vacuum for 5 minutes.
22) Engage pipette columns to the 96 channel head.
23) Move pipette columns in to the elution buffer (deck position 12).
24) Aspirate 130 μL of elution buffer at a flow rate of 0.3 ml/min and pause for 5 minutes to incubate.
25) Expel 130 μL of elution buffer at a flow rate of 9 ml/min with no pause.
26) If a second elution is needed, repeat steps 23-25 with a second Elution Buffer plate at deck position 14.

Example 8

Sample Prep Method Using an Electronic Pipette and a Manual Pipette

The following procedure is Semi Automated sample prep on an electronic pipette.

Procedure:

1) Transfer (Method A) 220 μL or (Method B) 370 μL of growth media containing appropriate selective agent to each well of a 96-well, deep well plate.
2) Inoculate each a single bacterial colony from a fresh plate.
3) Cover the plate with a gas permeable seal and shake at 300 rpm at 37° C. for 16 hours.

After 16 hours of growth, ~70 μL will evaporate. (Method A) will be left with 150 μL while (Method B) will be left with 300 μL.

4) Using regular pipette tips, transfer (Method A) 6 μL or (Method B) 12 μL of RNase A to the cell culture.
5) Using wide bore pipette tips, transfer (Method A) 150 μL or (Method B) 300 μL of lysis buffer to the cell culture.
6) Lyse the cells using 8 mix steps of 180 μL at a flow rate of 2 mL/min flow rate with 2 second pauses after each aspirate and each dispense step. Discard the tips.

7) Using wide bore pipette tips, transfer (Method A) 210 μL or (Method B) 420 μL of precipitation buffer to the lysed cells.
8) Precipitate the lysed cells using 8 mix steps 190 μL at a flow rate of 2 mL/min flow rate with 2 second pauses after each aspirate and each dispense step. Discard the tips.
9) Engage pipette columns.
10) Equilibrate pipette columns with 2 mix steps of 170 μL equilibration buffer (200 μL total volume in each well) using a flow rate of 0.78 ml/min with 5 second pause at the end of each aspirate and each dispense step.
11) Move pipette columns out of the equilibration buffer and aspirate 180 μL of air at 0.25 ml/min flow rate with 2 second pause.
12) Lower the pipette columns to the lysed, precipitated sample 1 mm from the bottom of the wells. Dispense 170 μL of air at 0.25 ml/min flow rate with 2 second.
13) Maintain the pipette columns at 1 mm above the bottom of the well. Capture the plasmid DNA using 12 mix steps (Method A) or 20 mix steps (Method B) of 180 μL at a flow rate of 0.25 ml/min with 10-20 second pauses at the end of each aspirate and each dispense step.
*Make sure that the columns do not come up (in Z direction) and stay at same position after step 12.
14) After capture step, move columns over the blotting station. Touch the Kimwipes on the blotting station to remove cell debris from the columns. Repeat once.
15) Move pipette columns into wash buffer. Wash the captured plasmid DNA with 2 cycles at 2 mL/min flow rate with 10 second pause.
16) Move pipette columns into wash buffer. Wash the captured plasmid DNA with 2 cycles at 2 mL/min flow rate with 10 second pause.
17) Move pipette columns into wash buffer. Wash the captured plasmid DNA with 2 cycles at 2 mL/min flow rate with 10 second pause.
18) Eject the pipette columns back into the column adaptor.
19) Move the adaptor carrying the columns to the vacuum drying station and apply vacuum for 5 minutes.
20) Engage pipette columns to the pipette head.
21) Move pipette columns in to the elution buffer.
22) Aspirate 130 μL of elution buffer at a flow rate of 0.3 ml/min and pause for 5 minutes to incubate.
23) Expel 130 μL of elution buffer at a flow rate of 9 ml/min with no pause.
24) Repeat steps 21-23 if second elution is needed with a second Elution Buffer plate at deck position 14.

The Following Procedure is an Example for a Manual Pipette.
Procedure:
1) Transfer (Method A) 150 μL or (Method B) 300 μL of growth media containing appropriate selective agent to 2.5 mL centrifuge tube.
2) Inoculate each a single bacterial colony from a fresh plate.
3) Close the cap of the centrifuge tube and shake at 300 rpm at 37° C. for 16 hours.
4) Using regular pipette tips, transfer (Method A) 6 μL or (Method B) 12 μL of RNase A to the centrifuge tube containing cell culture. Close cap and invert the centrifuge tube 5×.
5) Using regular pipette tips, transfer (Method A) 150 μL or (Method B) 300 μL of lysis buffer to the centrifuge tube containing cell culture.
6) Lyse the cells by inverting the centrifuge tube 20×.
7) Using regular pipette tips, transfer (Method A) 210 μL or (Method B) 420 μL of precipitation buffer to the lysed cells.
8) Precipitate the lysed cells by inverting the centrifuge tube 20×.
9) Engage pipette columns.
10) Dial the pipette setting to 170 μL and engage pipette tip columns. Make sure to attach the columns with pipette plunger down/pressed. Move the columns into a deep well block containing 200 μL of equilibrate buffer. Slowly release the plunger and wait until 170 μL has aspirated into the pipette tip column. Slowly press down on the plunger to dispense 170 μL of equilibration buffer. Repeat aspirate and dispense steps.
11) Move pipette columns out of the equilibration buffer and slowly aspirate 180 μL of air.
12) Lower the pipette columns to the lysed, precipitated sample 1 mm from the bottom of the centrifuge tube. Dispense 170 μL of air to move precipitants away from the bottom of the column.
13) Maintain the pipette columns at 1 mm above the bottom. Capture the plasmid DNA pipetting 170 μL aspirate and dispense steps. Perform 12 mix steps (Method A) or 20 mix steps (Method B) at very slow speed. Make sure liquid is being aspirated and dispensed through the column.
14) After capture step, clean off the end and side of the column of any cell debris from the columns.
15) Move pipette columns into wash buffer. Wash the captured plasmid DNA with 2 cycles of aspirate and dispense steps with slow pipetting.
16) Move pipette columns into wash buffer. Wash the captured plasmid DNA with 2 cycles of aspirate and dispense steps with slow pipetting.
17) Move pipette columns into wash buffer. Wash the captured plasmid DNA with 2 cycles of aspirate and dispense steps with slow pipetting.
18) Eject the pipette columns into the column adaptor. Attach adaptor to the vacuum pump and air dry the columns for 5 minutes.
19) Engage pipette columns to the pipette.
20) Move pipette columns in to the elution buffer with plunger depressed.
21) Aspirate 130 μL of elution buffer at a flow slowly. Let it sit for 5 minutes with elution buffer inside the column.
22) Expel 130 μL of elution buffer.
23) If a second elution is needed, repeat steps 20-22 with a second Elution Buffer plate at deck position 14.

What is claimed is:
1. A method for isolating plasmid DNA from cells in a liquid culture, comprising:
   a. providing a liquid culture comprised of growth medium and cells, wherein the cells contain plasmid DNA;
   b. lysing the cells in the liquid culture in the presence of the growth medium to produce a mixture, wherein the cells are lysed with alkali, and wherein the cells in the liquid culture are not centrifuged prior to lysis, and wherein lysozyme is not used for lysis;
   c. providing a pipette tip column; and
   d. passing at least a portion of the mixture through the pipette tip column, whereby a portion of the plasmid DNA is captured on the pipette tip column.
2. The method of claim 1, wherein the mixture is passed through the pipette tip column by repeated aspirate and expel steps.

3. The method of claim 2, wherein between step (b) and step (d), a chaotropic solution is added to the mixture, and wherein the pipette tip column is further comprised of a silica solid phase.

4. An automated method for isolating plasmid DNA from cells in a liquid culture, comprising:
   a. providing a liquid culture comprised of growth medium and cells, wherein the cells contain plasmid DNA;
   b. lysing the cells in the liquid culture in the presence of the growth medium to produce a mixture, wherein the cells in the liquid culture are not centrifuged prior to lysis;
   c. providing a pipette tip column; and
   d. passing at least a portion of the mixture through the pipette tip column, whereby a portion of the plasmid DNA is captured on the pipette tip column,
   wherein steps (b) and (d) are performed at pre-determined times.

5. The method of claim 4, wherein the mixture is passed through the pipette tip column by repeated aspirate and expel steps.

6. The method of claim 5, wherein between step (b) and step (d), a chaotropic solution is added to the mixture, and wherein the pipette tip column is further comprised of a silica solid phase.

7. The method of claim 4, wherein steps (a) and (b) are performed in a microplate.

\* \* \* \* \*